(12) United States Patent
Campbell et al.

(10) Patent No.: US 9,244,053 B2
(45) Date of Patent: Jan. 26, 2016

(54) APPARATUS FOR MONITORING AERATION IN FLUID OF HYDRAULIC CIRCUIT

(71) Applicant: Caterpillar Inc., Peoria, IL (US)

(72) Inventors: Hatuey D. Campbell, Peoria, IL (US); Shevon A. Vannitamby, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 402 days.

(21) Appl. No.: 13/889,584

(22) Filed: May 8, 2013

(65) Prior Publication Data

US 2014/0331742 A1 Nov. 13, 2014

(51) Int. Cl.
G01N 33/00 (2006.01)
G01N 33/28 (2006.01)

(52) U.S. Cl.
CPC .................. G01N 33/2841 (2013.01)

(58) Field of Classification Search
CPC ................................................ G01N 33/2835
See application file for complete search history.

(56) References Cited

U.S. PATENT DOCUMENTS

| | | | |
|---|---|---|---|
| 3,497,034 A | 2/1970 | Eddy, Jr. | |
| 5,361,582 A * | 11/1994 | Uchida et al. | 60/276 |
| 5,524,475 A * | 6/1996 | Kolpak et al. | 73/19.03 |
| 6,585,938 B1 | 7/2003 | Machida et al. | |
| 7,130,738 B2 | 10/2006 | Ha | |
| 2003/0136185 A1* | 7/2003 | Dutton et al. | 73/61.44 |
| 2004/0069051 A1* | 4/2004 | Hotta et al. | 73/61.41 |

FOREIGN PATENT DOCUMENTS

FR 2887633 12/2006

* cited by examiner

*Primary Examiner* — Laura Martin
*Assistant Examiner* — Alex Devito

(57) ABSTRACT

An apparatus for monitoring aeration in a fluid of a hydraulic circuit is provided. The apparatus includes at least two measuring units configured to connect at a first location, and a second location of the hydraulic circuit. The measuring units are configured to measure pressure, temperature, and density of the fluid at the respective locations. The apparatus further includes a computing unit configured to output aeration values of the fluid at the first and the second location based on the measured pressure, temperature, and density by the two measuring units. The apparatus further includes a correlation unit configured to correlate aeration levels at the first and second locations based on the measured aeration values.

13 Claims, 3 Drawing Sheets

APPARATUS FOR MONITORING AERATION IN FLUID OF HYDRAULIC CIRCUIT

TECHNICAL FIELD

The present disclosure relates to an apparatus for monitoring aeration in a fluid of a hydraulic circuit, and more particularly to an apparatus for monitoring aeration in oil used in an engine system.

BACKGROUND

Conventional methods and apparatus determine aeration of a fluid at one location in an engine system. The aeration value determined is indicative of the amount of air present in the fluid at that location. U.S. Published application Ser. No. 12/899,670 relates to a method and apparatus for measuring oil aeration of an engine. A density of pure oil and a density of air are calculated based on a measured oil pressure and a measured oil temperature of an oil line connecting a hydraulic pump of an engine and an oil gallery of a cylinder block. The oil aeration is then calculated based on a measured oil density, the measured oil pressure, the calculated density of the pure oil, and the calculated density of the air.

SUMMARY

In one aspect, the present disclosure provides an apparatus for monitoring aeration in a fluid of a hydraulic circuit. The apparatus includes at least two measuring units configured to connect at a first location, and a second location of the hydraulic circuit. The measuring units are configured to measure pressure, temperature, and density of the fluid at the respective locations. The apparatus further includes a computing unit configured to output aeration values of the fluid at the first and the second location based on the measured pressure, temperature, and density by the two measuring units. The apparatus further includes a correlation unit configured to correlate aeration levels at the first and second locations based on the measured aeration values.

In another aspect, the present disclosure provides an engine system including a tank configured to store oil, and an engine including an oil gallery configured to receive pressurized oil from the tank. The engine system further includes an apparatus configured to monitor aeration in oil at the tank and the oil gallery. The apparatus is coupled to the tank and the oil gallery. The apparatus includes a first measuring unit connected to the tank, and a second measuring unit connected to the oil gallery. The first and second measuring units are configured to measure pressure, temperature, and density of oil at the tank, and the oil gallery respectively. The apparatus further includes a computing unit configured to output aeration values of the oil at the tank and the oil gallery based on the measured pressure, temperature, and density by the first and second measuring units. The apparatus further includes a correlation unit configured to correlate aeration levels at the tank and the oil gallery based on the measured aeration values.

In another aspect, the present disclosure provides a method of monitoring aeration in a fluid of a hydraulic circuit. The method includes measuring pressure, temperature, and density of the fluid at a first location, and a second location of the hydraulic circuit. The method further includes computing aeration values of the fluid at the first and second locations based on the measured pressure, temperature, and density. The method further includes correlating aeration levels at the first and second locations based on the measured aeration values.

DETAILED DESCRIPTION

Reference will now be made in detail to specific embodiments or features, examples of which are illustrated in the accompanying drawings. Generally, corresponding or similar reference numbers will be used, when possible, to refer to the same or corresponding parts.

Aeration is a phenomenon wherein air or any gas is trapped in a fluid. In many cases, air may be trapped in the fluid when the fluid travels through complex, tortuous or narrow spaces that involve changes to flow-rates of the fluid and changes to temperature and pressure of the fluid, thereby resulting in a change in density of the fluid. These conditions are typically experienced in hydraulic systems such as, but not limited to, an engine, and a tank supplying a fluid, such as, but not limited to, oil.

In some cases, the phenomenon of aeration may be intrinsic to the hydraulic system due to system design thus leading to cavitation in the fluid. Conversely, air may be forcibly induced into fluids to cause aeration in a hydraulic circuit of various systems based on specific operating requirements. However, measurement of aeration in the fluid across one or more locations of the hydraulic circuit may allow engineers to analyze a behavior of the fluid across those locations while also diagnosing a constructional related performance of the hydraulic circuit of the system.

Figure 1:
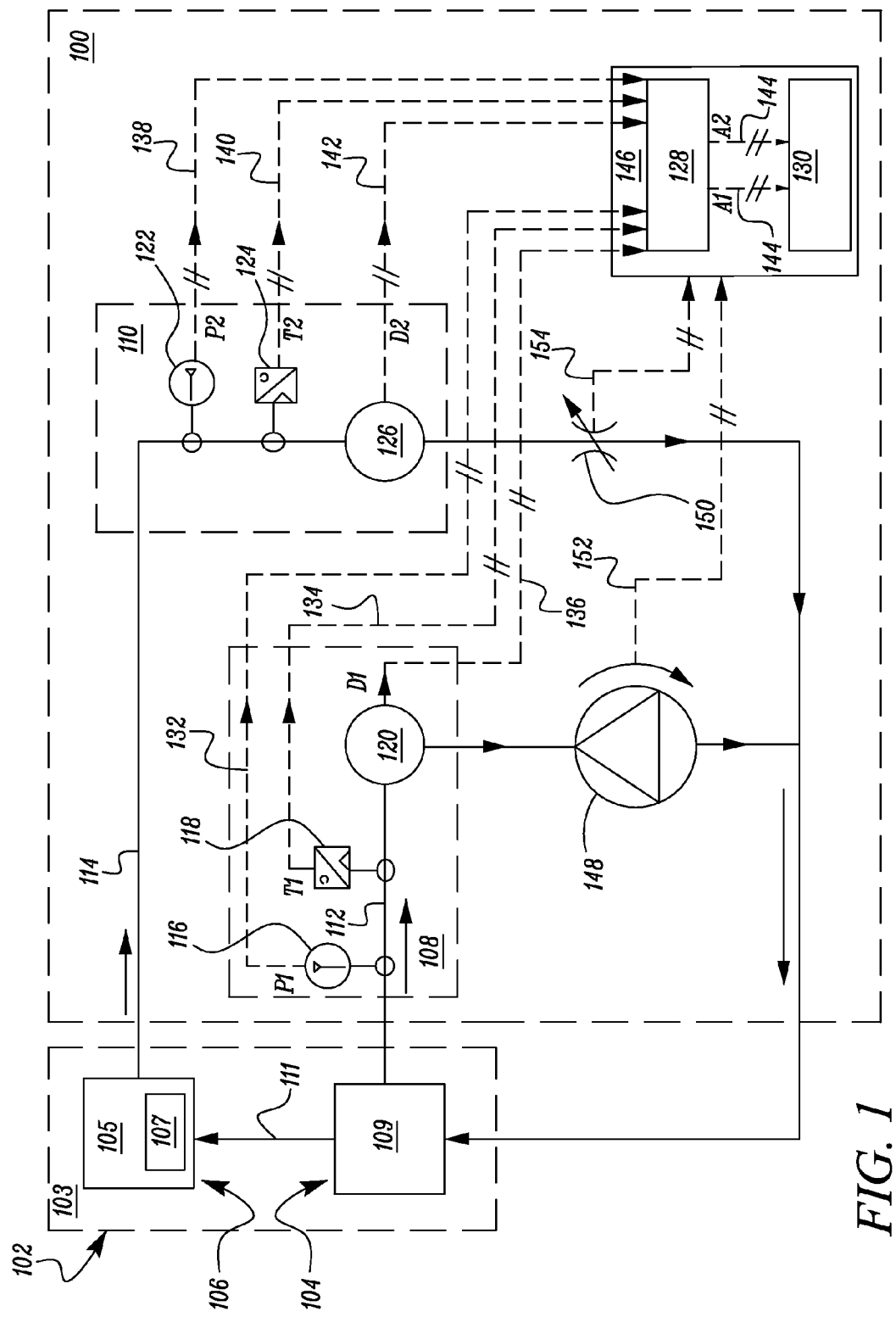
FIG. 1 illustrates a schematic of an exemplary apparatus employed in monitoring aeration in a fluid.

Referring to FIG. 1, a schematic of an exemplary apparatus 100 employed to monitor aeration in fluid in a hydraulic circuit 102 is illustrated. Boxes with dashed lines are used in the schematic to enclose components of elements such as the apparatus 100 and the hydraulic circuit 102. The hydraulic circuit 102 includes a first location 104 and a second location 106. The apparatus 100 includes a first measuring unit 108 and a second measuring unit 110 connected at the first location 104 and the second location 106 of the hydraulic circuit 102, respectively. The first and the second measuring units 108, 110 are configured to measure pressure, temperature, and density of the fluid at the first and the second locations 104, 106 respectively. A first conduit 112 fluidly connects the first measuring unit 108 to the first location 104 of the hydraulic circuit 102 while a second conduit 114 fluidly connects the second measuring unit 110 to the second location 106 of the hydraulic circuit 102. Solid lines are used in the schematic to represent fluid conduits.

The first measuring unit 108 includes a first pressure sensor 116, a first temperature sensor 118, and a first density sensor 120 disposed in the first conduit 112. The first pressure sensor 116 is configured to measure pressure $P_1$ of the fluid in the first conduit 112. The first temperature sensor 118 is configured to measure temperature $T_1$ of the fluid in the first conduit 112. The first density sensor 120 is configured to measure density $D_1$ of the fluid in the first conduit 112. The $P_1$, $T_1$, and $D_1$ of the fluid in the first conduit 112 are representative of pressure, temperature and density of the fluid at the first location 104 of the hydraulic circuit 102.

Similarly, the second measuring unit 110 includes a second pressure sensor 122, a second temperature sensor 124, and a second density sensor 126 disposed in the second conduit 114. The second pressure sensor 122 is configured to measure pressure $P_2$ of the fluid in the second conduit 114. The second temperature sensor 124 is configured to measure temperature $T_2$ of the fluid in the second conduit 114. The second density sensor 126 is configured to measure density $D_2$ of the fluid in the second conduit 114. The $P_2$, $T_2$, and $D_2$ of the fluid in the second conduit 114 are representative of pressure, temperature and density of the fluid at the second location 106 of the hydraulic circuit 102.

In an embodiment, the first and second pressure sensors 116, 122 may include, for example, pressure transducers configured to measure pressure of the fluid. The first and second temperature sensors 118, 124 may include, for example, thermocouples configured to measure temperature of the fluid. The first and second density sensors 120, 126 may include coriolis flow meters configured to measure density of the fluid. In alternative embodiments, other type of sensors known in the art, such as piezometers, manometers, strain gauges, pyrometers, thermistors, thermometers and other suitable devices may be used to determine the pressure, temperature, and the density of the fluid in the first and the second conduits 112, 114.

The first measuring unit 108 may be configured to generate signals indicative of the measured $P_1$, $T_1$ and $D_1$ at the first location 104 using the first pressure, temperature, and density sensors 116, 118, 118. The second measuring unit 110 may be configured to generate signals indicative of the measured $P_2$, $T_2$ and $D_2$ at the second location 106 using the second pressure, temperature, and density sensors 122, 124, 126.

The apparatus 100 includes a computing unit 128, and a correlation unit 130. The computing unit 128 is communicatively linked to the first measuring unit 108 and the second measuring unit 110 and may receive the measured $P_1$, $P_2$, $T_1$, $T_2$, $D_1$, and $D_2$. Dashed lines with hatch marks are used in the schematic to represent communicative links.

In the embodiment illustrated, a first communication link 132 communicatively connects the first pressure sensor 116 with the computing unit 128 a second communication link 134 communicatively connects the first temperature sensor 118 with the computing unit 128, and a third communication link 136 communicatively connects the first density sensor 120 to the computing unit 128. A fourth communication link 138 communicatively connects the second pressure sensor 122 with the computing unit 128, a fifth communication link 140 communicatively connects the second temperature sensor 124 with the computing unit 128, and a sixth communication link 142 communicatively connects the second density sensor 126 to the computing unit 128.

The computing unit 128 is configured to compute and generate signals indicative of aeration values $A_1$, $A_2$ of the fluid at the first and second locations 104, 106 based on the measured $P_1$, $P_2$, $T_1$, $T_2$, and $D_1$, $D_2$ of the fluid by the first and the second measuring units 108, 110. In various embodiments of the present disclosure, the computing unit 128 may include one or more of modulation curves, data tables, and/or module maps representative of parameters of the fluid under various conditions of temperature, and pressure.

The correlation unit 130 is communicatively connected to the computing unit 128 via a seventh communication link 144. The correlation unit 130 is configured to simultaneously receive the aeration valves $A_1$, $A_2$ at the first and the second locations 104, 106. The correlation unit 130 is configured to correlate aeration values $A_1$, $A_2$ of the fluid at the first and second locations 104, 106 and provide various trends indicative of a relationship such as, positive, negative, or zero, between the aeration level in the fluid and the various components used in the hydraulic circuit 102. In some embodiments, the correlation unit 130 may generate the trends such as, scatter diagrams, histograms, bar graphs, data tables, and/or module maps by dynamically plotting the aeration values of fluid in the first and second conduits 112, 114, representative of the aeration values of the fluid at the first and second locations 104, 106.

In one embodiment, the computing unit 128 and the correlation unit 130 may integrally reside on a data acquisition system DAS 146. The DAS 146 may embody a general purpose computer having a storage device such as but not limited to a hard disk, ROM, RAM, and the like. The DAS 146 may store the measured $P_1$, $P_2$, $T_1$, $T_2$, and $D_1$, $D_2$ of the fluid received from the first and second measuring units 108, 110 the aeration values from the computing unit 128, and the correlation data from the correlation unit 130.

The apparatus 100 may include a pump 148 disposed in the first conduit 112 and located downstream of the first measuring unit 108. The pump 148 may be configured to deliver the fluid from the first location 104 to the first measuring unit 108. The pump 148 may assist in maintaining a steady flow rate of fluid in the first conduit 112 for purposes of measurement, and in returning the fluid back to the first location 104.

The apparatus 100 may include a flow control valve 150 configured to control a flow rate of the fluid across the second measuring unit 110 such that measurement of pressure, temperature, and density of oil at the second location 106 is observed under steady flow rates. In the embodiment illustrated the flow control valve 150 is fluidly connected with the second measuring unit 110 and the second location 104 and may include a one-way valve configured to restrict flow of fluid from the first conduit 112 into the second conduit 114 via the pump 148.

The apparatus 100 may include an eighth and ninth communication link 152, 154 communicatively connecting the DAS 146 to the pump 148 and the flow control valve 150 respectively. The eighth and ninth communication links 152, 154 may be configured to send control signals from the DAS 146 to the pump 148 and the flow control valve 150 to operatively control the pump 148 and the flow control valve 150. In some embodiments, the eighth and ninth communication links 152, 154 may be configured to communicate data pertaining to operational health of the pump 148 and the flow control valve 150 to the DAS 146. The DAS 146 may be configured to diagnostically monitor performance of the apparatus 100 as a function, at least in part, of the operational health data. The DAS 146 may configure the first and second measuring units 108, 110 of the apparatus 110 to obtain pressure, temperature, and density of the fluid under steady flow conditions based on the health data.

In one exemplary embodiment, the apparatus 100 may be employed in an engine system 103 consisting of a tank 109, and an engine 105 including an oil gallery 107. The first location 104 may include the tank 109 and the second location 106 may include the oil gallery 107. The tank 109 may be configured to store oil and supply oil to the engine 105 while the oil gallery 107 may be configured to receive pressurized oil from the tank 109 via an engine oil circuit 111 and lubricate one or more reciprocating and rotating parts of the engine 105. The first conduit 112 may fluidly connect the first measuring unit 108 to the tank 109. The second conduit 114 may fluidly connect the second measuring unit 110 to the oil gallery 107. In other embodiments, the apparatus 100 and methods disclosed may be applied to other hydraulic circuits known in the art.

Figure 2:
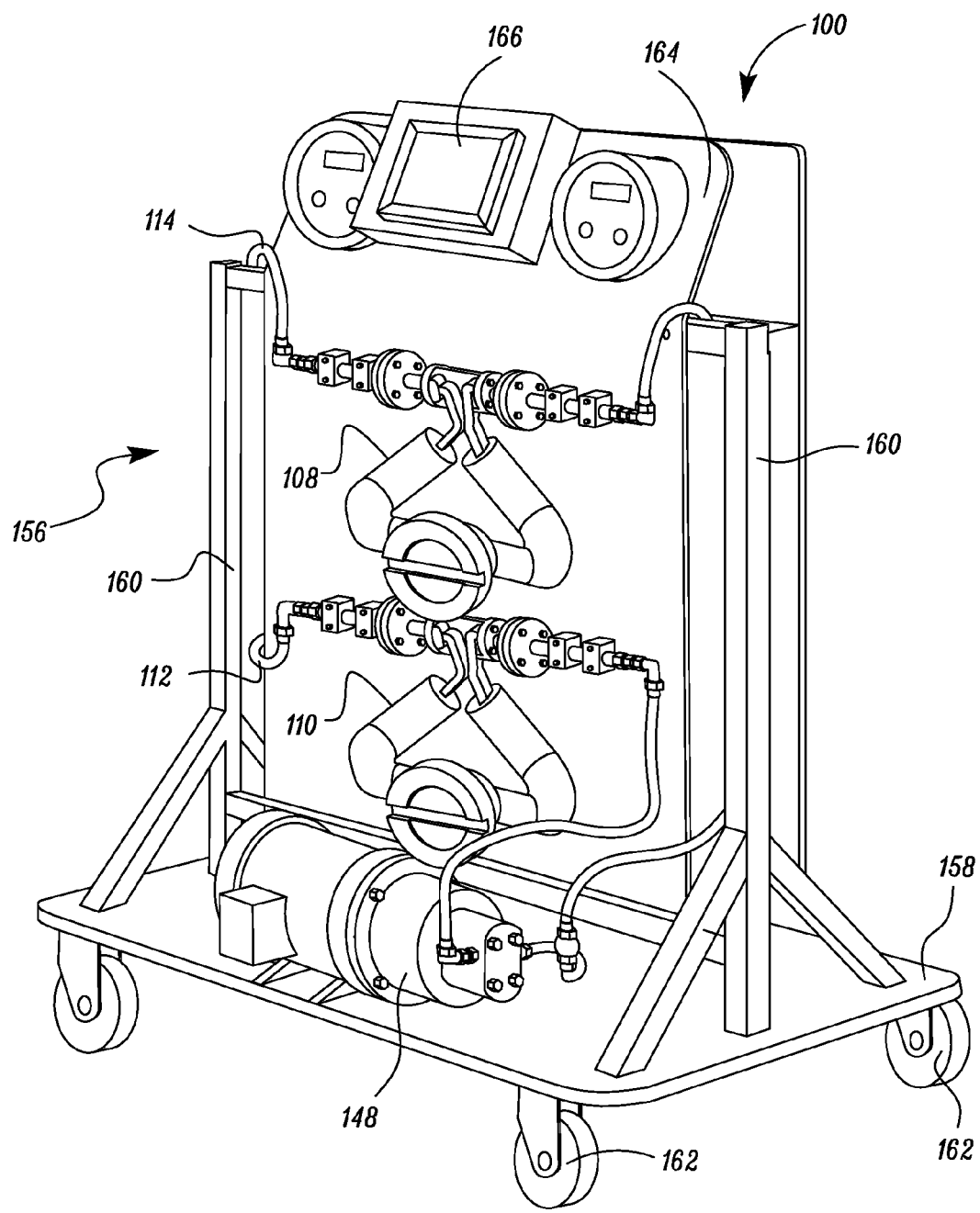
FIG. 2 illustrates a perspective view of the exemplary apparatus employed in monitoring aeration in a fluid.

Referring to FIG. 2, an exemplary embodiment of the apparatus 100 configured as a plug-and-play type of apparatus to monitor the aeration in the oil circulated between the tank 109 and the oil gallery 107 of an engine 105 or another embodiment of the hydraulic circuit 102 is illustrated. The apparatus 100 may be mounted on a frame 156 including a base 158, and a pair of upright support members 160 attached on the base 158. The frame 156 could include caster wheels 162 mounted underneath the base 158 such that the apparatus 100 may be moved from one location to another location for carrying out measurement of aeration, for example, the apparatus 100 may be moved on-site and positioned on any machine to measure aeration at the tank 109 and the oil gallery 107 therein. The first and the second measuring units 108, 110, may be secured to the pair of upright support members 160 while the pump 148 may be secured on the base 158 of the frame 156. The first and second conduits 112, 114 may include flexible hose pipes configured to connect the first and second measuring units 108, 110, to the tank 109 and the oil gallery 107 of the engine 105 respectively.

In one embodiment, the DAS 146 may be rigidly secured to a board 164 extending between the pair of upright support members 160 of the frame 156. In one embodiment, the DAS 146 may include one or more display devices 166 configured to display aeration values to an operator. However, in another embodiment, the DAS 146 may be located at an operator station situated off-site. In this embodiment, the first and second measuring units 108, 110 may be wirelessly connected with the DAS 146 using wireless communication channels to communicate measurement signals and/or control signals associated with various operations of the apparatus 100.

In an alternative embodiment, the apparatus 100 may be integrated with the engine 105 and the tank 109 to form the engine system 103 of the present disclosure. The first pressure, temperature, and density sensors 116, 118, 120 of the first measuring unit 108 may be disposed in the tank 109, and the second pressure, temperature, and density sensors 122, 124, 126 of the second measuring unit 110 may be disposed in the oil gallery 107 of the engine 105. The apparatus 100 may be configured to provide continuous real-time measurement values to an operator during operation of the engine 105 and the tank 109.

Although the apparatus 100 in the illustrated embodiment is configured to operate as a stand-alone device via the plug-and-play configuration, an ordinary person skilled in the art will recognize that the apparatus 100 may also be integrated with the engine 105 and the tank 109 of the engine system 103 such that the engine system 103 is configured to include the apparatus 100 therein. In this manner, the engine 105, the tank 109, and the apparatus may be packaged to form a compact engine system 103 capable of monitoring aeration in the engine 105 and the tank 109.

INDUSTRIAL APPLICABILITY

Figure 3:
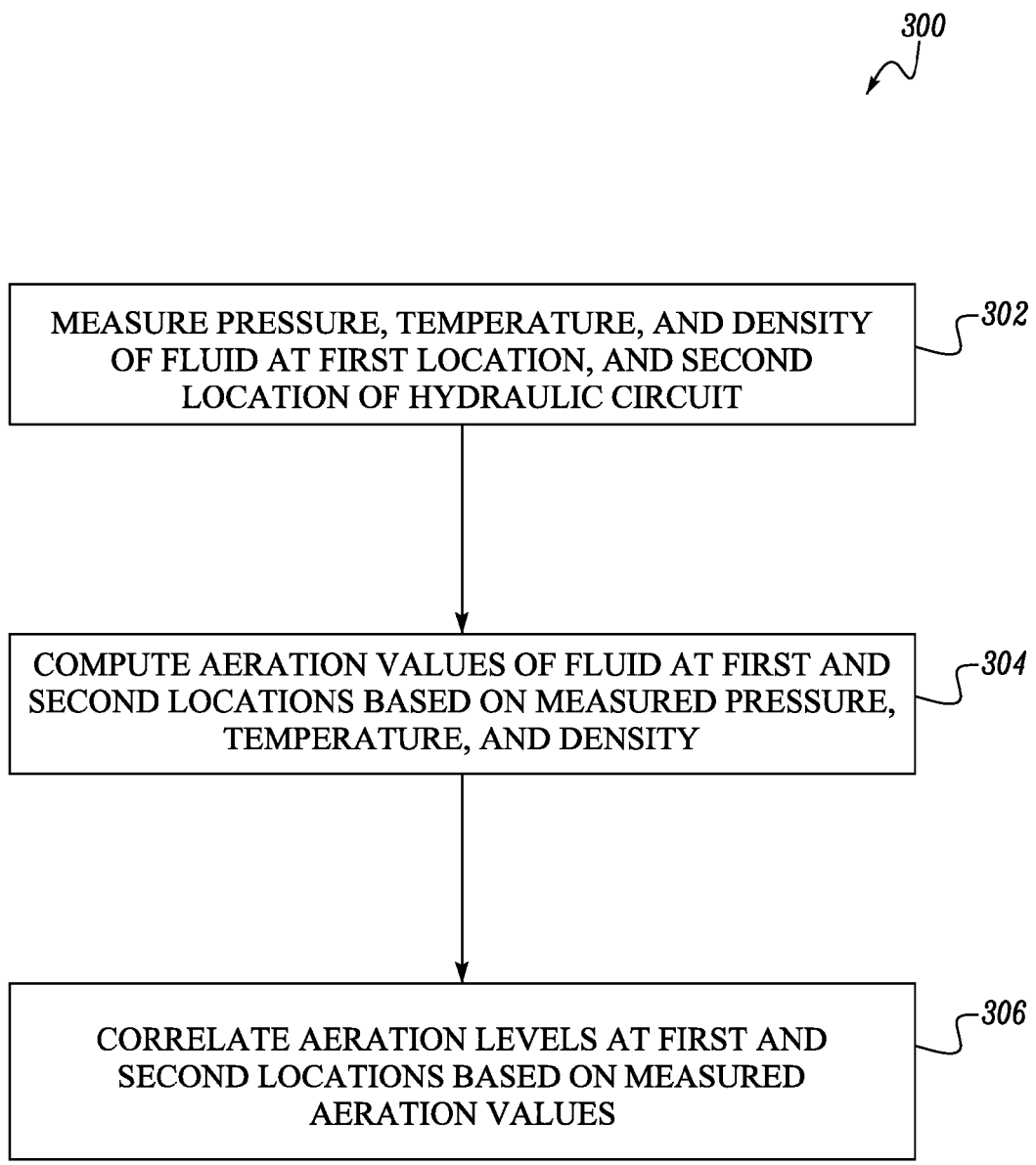
FIG. 3 illustrates a flowchart of an exemplary method of monitoring aeration in a fluid of a hydraulic circuit.

FIG. 3 illustrates a method 300 of monitoring aeration in a fluid of the hydraulic circuit 102. At step 302, the method 300 includes measuring pressure $P_1$, $P_2$, temperature $T_1$, $T_2$, and density $D_1$, $D_2$ of the fluid at the first location 104, and the second location 106 of the hydraulic circuit 102. In an embodiment, the method 300 includes receiving the measured pressure $P_1$, $P_2$, temperature $T_1$, $T_2$, and density $D_1$, $D_2$ of the fluid from the first and second measuring units 108, 110, at the DAS 146. The first and second measuring units 108, 110, being associated with the first location 104 and the second location 106, respectively. In an embodiment, the method 300 includes delivering fluid from the first location 104 to the first measuring unit 108 by the pump. In another embodiment, the method 300 further includes controlling the flow rate of the fluid past the second measuring unit 114 associated with the second location 106.

At step 304, the method 300 includes computing aeration values of the fluid at the first and second locations 104, 106, based on the measured pressure, temperature, and density.

In an embodiment, the method 300 includes determining the density of air $D_{a1}$, $D_{a2}$ and the density of pure fluid $D_{f1}$, $D_{f2}$ at the first and the second locations 104, 106, based on the pressure $P_1$, $P_2$ and temperature $T_1$, $T_2$ of the fluid at the first and the second locations 104, 106, respectively. In one embodiment, the computing unit 128 may include a microprocessor programmed to execute mathematical models and obtain the densities of air $D_{a1}$, $D_{a2}$ and densities of pure fluid $D_{f1}$, $D_{f2}$ at the first location 104, and the second location 106 from the measured pressures $P_1$, $P_2$ and temperatures $T_1$, $T_2$. Exemplary mathematical models may be represented in the equations 1-4 as follows:

$$D_{a1} = P_1 * P_{atm} / R * T1 + 273 \qquad \text{eq. 1;}$$

$$D_{a2} = P_2 * P_{atm} / R * T2 + 273 \qquad \text{eq. 2;}$$

wherein $P_{atm}$ is atmospheric pressure; and
R is ideal gas constant.

The density of pure fluid $D_{f1}$, $D_{f2}$ may be determined by the computing unit 128 based on specific oil densities at the temperatures $T_1$, $T_2$ measured at the oil gallery 107, and the tank 109 using the following exemplary equations:

$$D_{f1} = -0.64 * T_1 + X \qquad \text{eq. 3;}$$

$$D_{f2} = -0.64 * T_2 + X \qquad \text{eq. 4;}$$

wherein X is a constant and is known for a given fluid, for example X=884.6 for oil.

The aeration in the fluid $A_1$, $A_2$ can be determined by the computing unit 128 based on the density of the pure fluid $D_{f1}$, $D_{f2}$, density of fluid and air mixture $D_1$, $D_2$, and densities of air $D_{a1}$, $D_{a2}$ measured at the first and second locations 104, 106 for given pressures $P_1$, $P_2$ and temperatures $T_1$, $T_2$. In one embodiment, the method 300 includes measuring the density of the fluid and air mixture $D_1$, $D_2$ by a coriolis flow meter. Exemplary relations to obtain aeration from the aforesaid variables may be given by equations 5 and 6 as follows:

$$A_1 = D_{f1} - D_1 / D_1 - D_{a1} * \qquad \text{eq. 5;}$$

$$A_2 = D_{f2} - D_2 / D_2 - D_{a2} * \qquad \text{eq. 6;}$$

where $D_{a1}$, and $D_{f1}$ is determined in equations 1, and 3 respectively while $D_{a2}$, and $D_{f2}$ is determined in equations 2, and 4 respectively.

The DAS 146 may receive the measured pressure $P_1$, temperature $T_1$, and density $D_1$ of the fluid from the first measuring unit 108. The computing unit 128 of the DAS 146 may then calculate the aeration value $A_1$ of oil at the oil gallery 107 using equations 1, 3, and 5. Similarly, the second measuring unit 110 measures the pressure $P_2$, temperature $T_2$, and density $D_2$ of the fluid at the second location 106 and the computing unit 128 may compute the aeration value $A_2$ of fluid at the second location 106 using equations 2, 4, and 6.

At step 306, the method 300 includes correlating aeration levels at the first and second locations 104, 106, and output various the trends for understanding the relationship between the aeration level in the fluid and design of various components in the hydraulic circuit 102. Measurement of aeration in the fluid at two locations of the hydraulic circuit 102 aids in correlating and monitoring aeration at the two locations. In one embodiment, a first one of the two locations is assumed to be a reference location where the fluid is operating under ambient temperature and pressure conditions. The reference value of aeration at the first one of the two locations serves in analyzing a change in the aeration value of the fluid at a second one of the two locations. The aeration levels may then be correlated to study and improve a system design of components forming the hydraulic circuit 102, modify fluid properties, adjust operating temperatures or pressures at the first and second locations 104, 106.

In an exemplary embodiment, under an ideal operating condition, the method 300 may assume the aeration level at the oil gallery 107 is substantially similar to the aeration level at the tank 109. Further, while simultaneously receiving the aeration valves $A_1$, $A_2$ at the tank 109 and the oil gallery 107, the trends may provide understanding the relationship between the aeration levels in the oil at the oil gallery 107 and engine speed, loading condition, design of the engine oil circuit 111 etc. The trends such as, scatter diagrams, histograms, bar graphs, data tables, and/or module maps may be displayed to an operator using the display devices 166 of the apparatus 100.

It will apparent to a person having ordinary skill in the art the correlation unit 130 may provide an indication of a dependency of the aeration levels on the engine speed, or loading condition of the engine 105, or design of the engine oil circuit 111. Thus, the apparatus 100 is able to provide useful insight to an operator to design the engine oil circuit 111, identify optimal engine speed/loading condition to maintain aeration levels within a pre-determined level.

Although the apparatus 100 has been employed at two locations of the hydraulic circuit 102, in another embodiment, the apparatus 100 may be connected across a specific component of the hydraulic circuit 102 to measure aeration level of the fluid entering and leaving the component. In this manner, aeration induced into or disappearing from the fluid by the component be detected and a system design of that specific component may be studied or analyzed.

From the foregoing disclosure it will be appreciated that, although specific embodiments have been described herein for purposes of illustration, various modifications or variations may be made without deviating from the spirit or scope of inventive features claimed herein. Other embodiments will be apparent to those skilled in the art from consideration of the specification and figures and practice of the arrangements disclosed herein. It is intended that the specification and disclosed examples be considered as exemplary only, with a true inventive scope and spirit being indicated by the following claims and their equivalents.

We claim:

1. An apparatus for monitoring aeration in a fluid of a hydraulic circuit, the apparatus comprising:
    at least two measuring units configured to connect at a first location, and a second location of the hydraulic circuit, the measuring units configured to measure pressure, temperature, and density of the fluid at the respective locations;
    a flow controller disposed after one of the measuring units, the flow controller configured to control a flow rate of the fluid from one of the first and second locations across one of the at least two measuring units;
    a computing unit configured to output aeration values of the fluid at the first and the second location based on the measured pressure, temperature, and density by the two measuring units; and
    a correlation unit configured to correlate aeration levels at the first and second locations based on the measured aeration values.

2. The apparatus of claim 1, wherein the computing unit and the correlation unit reside on a data acquisition unit.

3. The apparatus of claim 1, wherein the measuring unit configured to measure density is a coriolis flow meter.

4. An engine system including:
    an engine including an oil gallery;
    a tank fluidly connected to the oil gallery and configured to supply fluid to the oil gallery; and
    the apparatus of claim 1, configured to monitor aeration in the fluid supplied from the tank to the oil gallery of the engine.

5. An engine system comprising:
    a tank configured to store oil;
    an engine including an oil gallery configured to receive pressurised oil from the tank; and
    an apparatus coupled to the tank and the oil gallery of the engine, the apparatus configured to monitor aeration in oil at the tank and the oil gallery, the apparatus including:
        a first and a second measuring unit connected to the oil gallery, and the tank respectively, the measuring units configured to measure pressure, temperature, and density of oil at the oil gallery and the tank;
        a flow controller disposed after the first measuring unit, the flow controller configured to control a flow rate of the oil from the oil gallery across the first measuring unit;
        a computing unit configured to output aeration values of the oil at the oil gallery and the tank based on the measured pressure, temperature, and density by the first and second measuring units; and
        a correlation unit configured to correlate aeration levels at the oil gallery and the tank based on the measured aeration values.

6. The engine system of claim 5, wherein the computing unit and the correlation unit reside on a data acquisition unit.

7. The engine system of claim 5, wherein the measuring units configured to measure density are coriolis flow meters.

8. The engine system of claim 5 further including a pump associated with the second measuring unit, the pump configured to deliver fluid from the tank to the second measuring unit.

9. A method of monitoring aeration in a fluid of a hydraulic circuit, the method comprising:
    measuring pressure, temperature, and density of the fluid at a first location, and a second location of the hydraulic circuit;
    controlling a flow rate of the fluid past a first measuring unit associated with the first location;
    computing aeration values of the fluid at the first and second locations based on the measured pressure, temperature, and density; and
    correlating aeration levels at the first and second locations based on the measured aeration values.

10. The method of claim 9 further including receiving the measured pressure, temperature, and density of the fluid from the first measuring unit, and a second measuring unit at a data acquisition unit, the first and second measuring units associated with the first location, and the second location respectively.

11. The method of claim 9 wherein computing aeration values further includes determining density of air at the first and the second location based on the pressure, and the temperature at the first and the second locations respectively.

12. The method of claim 10 further including delivering the fluid from the second location to the second measuring unit by a pump.

13. The method of claim 9, wherein measuring the density of the fluid includes measuring the density of the fluid by a coriolis flow meter.

* * * * *